Feb. 26, 1974 L. E. GAVELLO Plant Pat. 3,494
HEBE (VERONICA) PLANT
Filed Oct. 19, 1972
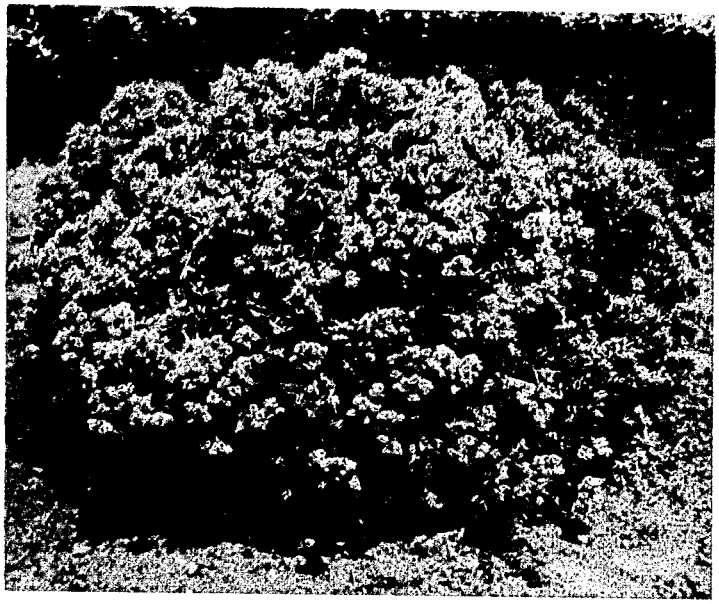
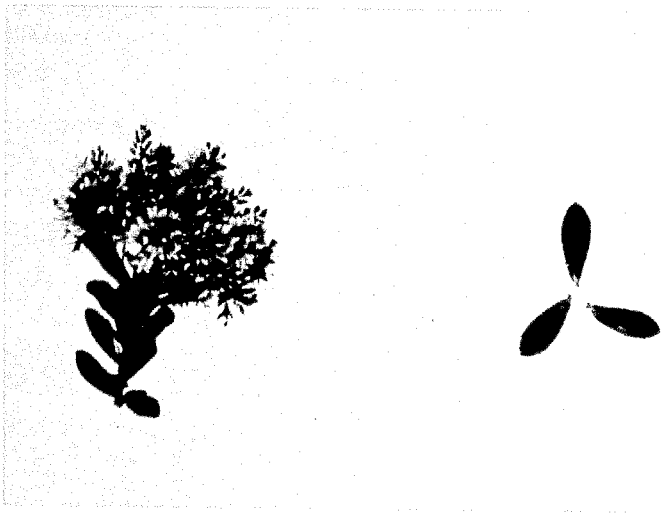

United States Patent Office

Plant Pat. 3,494
Patented Feb. 26, 1974

3,494
HEBE (VERONICA) PLANT
Louis E. Gavello, 3436 Maricopa Ave.,
Richmond, Calif. 94804
Filed Oct. 19, 1972, Ser. No. 299,121
Int. Cl. A01h 5/00
U.S. Cl. Plt.—54 1 Claim My invention relates to a new and distinct variety of Hebe (Veronica) plant discovered growing in my growing grounds at 29th and Salesian Avenue, in Richmond, Calif. The plant appeared in a block of about 200 five gallon can sized plants of Hebe "Bonete" (Plant Pat. No. 2,720) and Hebe "Desi Lor" and is characterized by the distinctly blue color of the blossoms and the compact habit of growth, which contrast quite strikingly with other Hebes of which I am aware.

The parentage of this new and distinctive variety of Hebe is unknown to me, but appears to be a chance hybrid between Hebe "Bonete" and Hebe "Desi Lor." The new seedling was discovered in the fall of 1967, growing in the previously defined area containing Hebe "Bonete" and Hebe "Desi Lor," which had blossomed and set seed.

This area is level land about three miles from San Francisco Bay where the climate is generally cool coastal type with mild winters and summers cooled by coastal fog.

The plant was first asexually reproduced by me in May of 1968, in the same growing grounds previously described, from softwood (medium soft) cuttings rooted in coarse sand. Fifty of such asexual reproductions were made in May of 1968 and seventy-five in May of 1969, with the number of generations, two.

The plant grows in lush form, about 3 feet tall, with a spread of the order of 4½ feet, and is loosely compact and mounding with short erect branches, reaching maturity with a medium rate of growth, in approximately four years.

The accompanying drawing shows, in separate views, a typical bush of my new variety of Hebe plant, a number of racemes on a branch, and specimens of individual leaves, all depicted in color as nearly true as it is reasonably possible to make the same in a color illustration of this character.

FOLIAGE

The foliage is evergreen, the leaves having the following characteristics:

*Shape of leaf.*—Elliptic obovate, narrowing toward the base;
*Size.*—Blades 1½ to 3 cm. long on petioles 1 to 3 mm. long;
*Texture.*—Glabrous on upper side, smooth beneath;
*Color.*—American Green (Plate 22, A–7) upper side, jade green lower side;
*Ribs and veins.*—Prominent midrib from base to tip, first lateral veins obscure;
*Margin.*—Entire to minutely and irregularly toothed;
*Leaf Arrangement.*—Opposite.

FLOWERS

The flowers are held in compact axiallary panicles on single peduncle 1¼ to 1¾ inches long, near the ends of branches. The form of panicle is broadly conical approximately 1¾ inches at the base and tapering to the tip. Each fully developed cluster, approximately eight panicles, is 4 to 5 inches across.

FLORETS

The florets are on the slender pedicels 2 to 5 mm. long and have the following additional characteristics:

*Form.*—4 sepals, 4 petals, 2 laterals wing-like, the upper slightly broader than the lower;
*Size.*—Corollas are about 7 mm. long, lobes spreading, about 10 mm. across;
*Color.*—Between Columbine Blue and Violine (Plate 42, page 107) (Maerz & Paul dictionary of color, 2nd Edition 1950).

FILAMENTS AND ANTHERS

Stamens—two in number, filaments slender, exserted about 2 to 3 mm., another versatile, about 1 mm. long.

BUDS

The buds are conical, about 3 mm. long, the sepals being slight imbricate.

BLOOMS

The plant blooms from April to the end of June, in Central California, San Francisco Bay area, and repeats in early October and lasts until the beginning of frost.

WEATHER RESISTANCE

This plant grows best in full sun along the cool coastal area, or at least three hours daily of direct sun. Inland it would probably require partial shade or filtered sun.

DISEASE RESISTANCE

The plant is free of major diseases.

Having described and illustrated my new variety of Hebe (Veronica) plant, I claim:

1. A new and distinct variety of Hebe (Veronica) plant, substantially as illustrated and described and characterized as to novelty by:
   (a) the compact mounding form of the plant having a low height and a spread greater than its height
   (b) the distinct bluish color of the profuse flowers covering the tips of the foliage
   (c) the long and repeated blooming period
   (d) its resistance to weather and disease
   (e) its moderate growth and controlled habit making it suitable for garden ornament as massed blue flowering shrubs.

No references cited.

ROBERT E. BAGWILL, Primary Examiner